US00PP24574P3

(12) United States Plant Patent
Egger

(10) Patent No.: US PP24,574 P3
(45) Date of Patent: Jun. 24, 2014

(54) ***HEUCHERA* PLANT NAMED 'GALAXY'**

(50) Latin Name: ***Heuchera* hybrid**
Varietal Denomination: Galaxy

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 223 days.

(21) Appl. No.: 13/507,430

(22) Filed: Jun. 27, 2012

(65) Prior Publication Data

US 2014/0007310 P1 Jan. 2, 2014

(51) Int. Cl.
*A01H 5/00* (2006.01)

(52) U.S. Cl.
USPC ..... Plt./440

(58) Field of Classification Search
CPC ..... A01H 5/02; A01H 5/12
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by leaves that are red brown with hot pink spots in spring and when new to almost black with pink spots in older leaves summer through winter medium large, glossy leaves, well branched, medium large, mounding habit, and excellent vigor.

3 Drawing Sheets

Botanical denomination: *Heuchera* hybrid.
Variety designation: 'Galaxy'.

BACKGROUND OF THE INVENTION

The present invention relates to a new and distinct cultivar of *Heuchera* and given the cultivar name of 'Galaxy'. *Heuchera* is in the family Saxifragaceae. *Heuchera* 'Galaxy' originated from a cross between *Heuchera* K428-5, a proprietary non-commercial hybrid, as the seed parent, and *Heuchera* K428-11, a proprietary non-commercial hybrid, as the pollen parent.

Compared to the seed parent, *Heuchera* K428-5, the new cultivar has glossy red brown, rather than dull brown, spring leaves.

Compared to the pollen parent, *Heuchera* K428-11, the new cultivar has a larger habit and larger leaves.

Compared to *Heuchera* 'Midnight Rose', U.S. Plant Pat. No. 18,551, the new cultivar has leaves that are red brown with pink spots rather than black with pink spots, a larger habit, larger leaves, and fewer and shorter inflorescences.

This new *Heuchera* is uniquely distinguished by:

1. leaves that are red brown with hot pink spots in spring and when new to almost black with pink spots in older leaves summer through winter,
2. medium large, glossy leaves,
3. well branched, medium large, mounding habit,
4. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
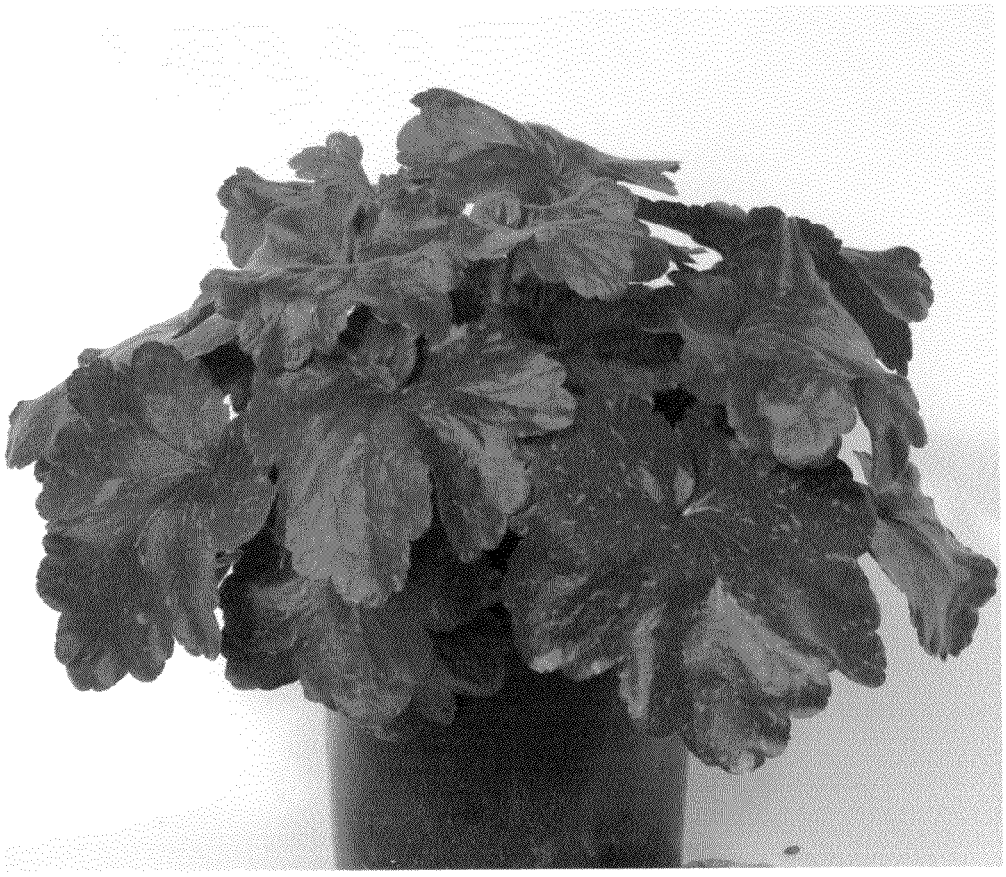
FIG. 1 shows a one-and-a-half-year-old plant of *Heuchera* 'Galaxy' growing in a two gallon container, grown in a cool greenhouse, in May in Canby, Oreg.
Figure 2:
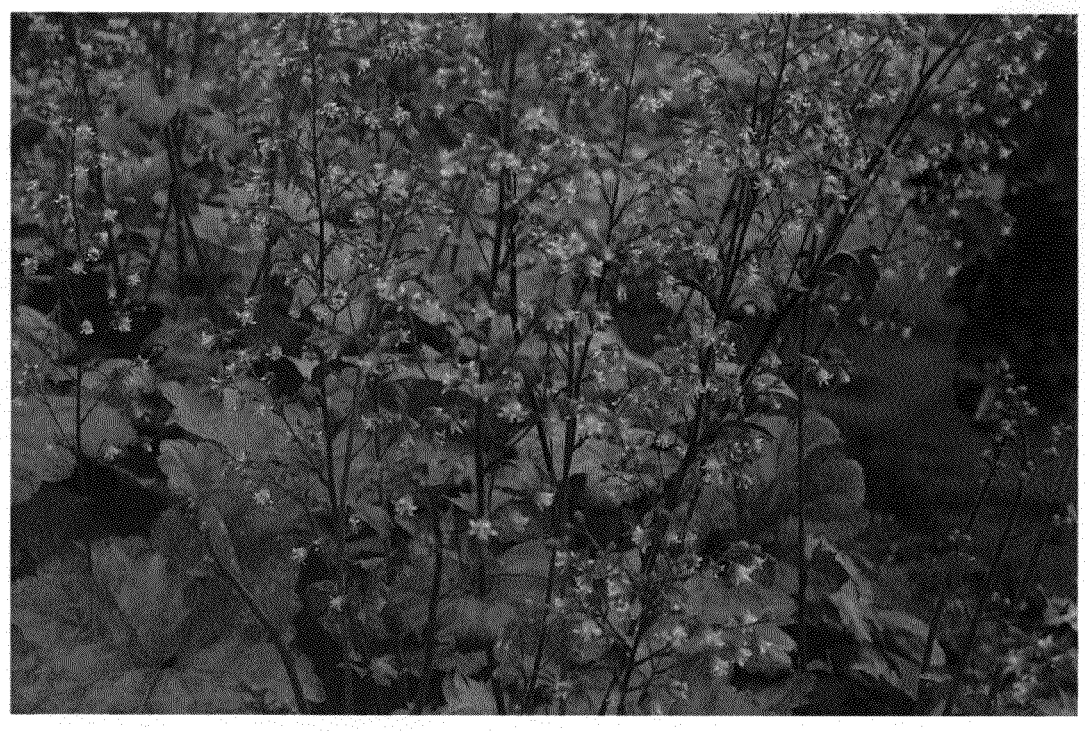
FIG. 2 shows the new cultivar in bloom, growing outside in a trial bed early in June in Canby, Oreg.
Figure 3:
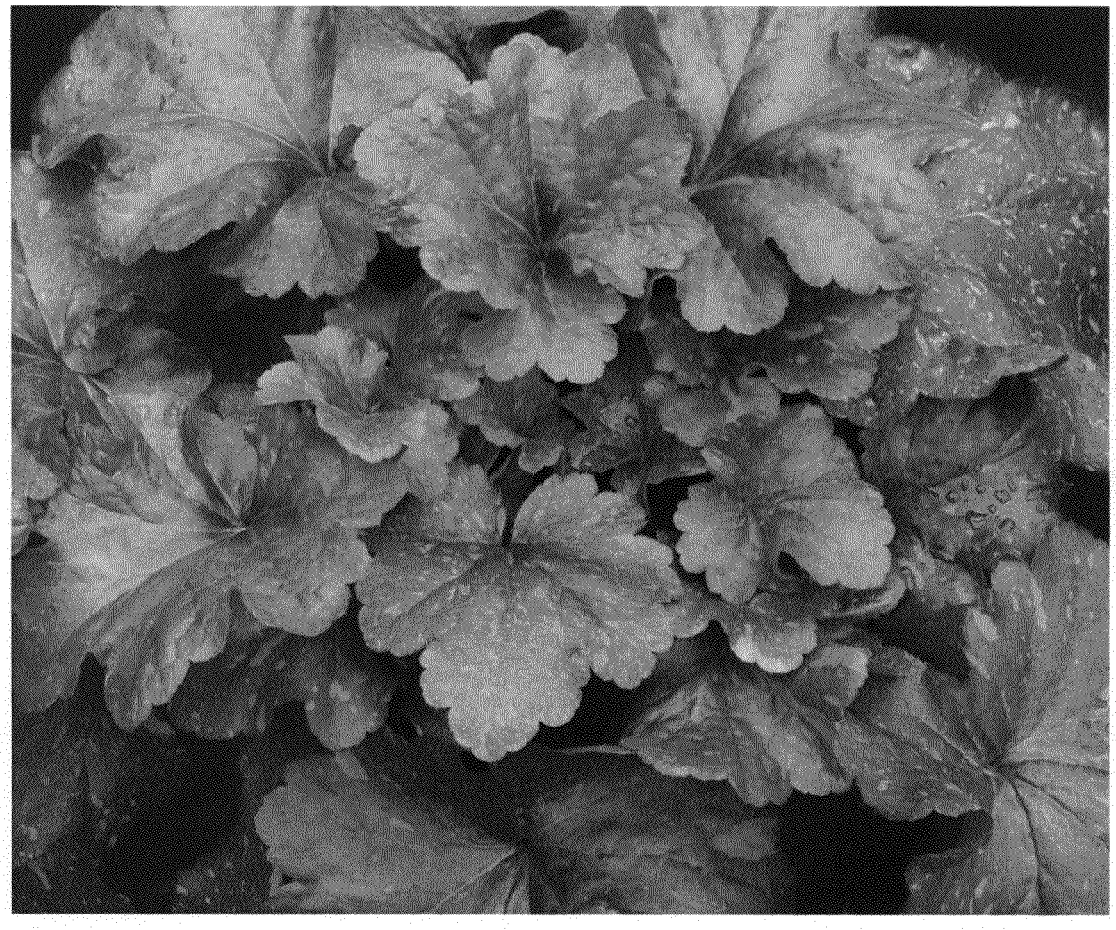
FIG. 3 shows a close up of the new cultivar grown in a cold greenhouse in the middle of May in Canby, Oreg.

The following is a detailed description of the new *Heuchera* cultivar based on observations taken in April of one-and-a-half-year-old specimens growing in one gallon containers, grown in a cool greenhouse, in late May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart.* $5^{th}$ edition.

Plant:

*Form.*—Basal rosette, herbaceous perennial.
*Hardiness.*—USDA Zone 4 to 9.
*Size.*—27 cm tall from top of the foliage to the ground and 52 cm wide.
*Habit.*—Mounding.
*Vigor.*—Excellent.

Leaf:

*Type.*—Simple.
*Arrangement.*—Rosette.
*Shape.*—Ovate to orbicular.
*Lobing/division.*—7 shallow lobes, shallow secondary lobes.
*Venation.*—Palmate.

*Margins*.—Broadly crenate.
*Apex*.—Mucronulate.
*Base*.—Cordate, lobes sometime overlapping at the base.
*Blade size*.—Grows to 17 cm long and 16 cm wide.
*Texture*.—Leathery.
*Surface texture*.—Glandular pubescent on both sides.
*Petiole description*.—Grows to 19 cm long and 3 mm wide, glandular hairs, Greyed Purple 187B.
*Leaf color*.—Variable, depending on light and temperature; spring topside Greyed Purple 184A with spots Red Purple 68A, bottom side Red Purple 59A; summer and fall topside, new leaves are Greyed Purple 187B with spots Red Purple 68A, bottom side Red Purple 59A; winter and mature leaves topside are closest to Greyed Purple N186A with spots Red Purple 68C, bottom side Purple N79A.

Inflorescence:
*Size*.—Grows to 4 cm wide and 7 cm long.
*Type*.—Thyrse.
*Number of flowers per thyrse*.—About 40.
*Number of thyrse*.—About 3 in the first spring flush.
*Peduncle*.—Grows to 40 cm long and 3.5 mm wide at base, Greyed Purple 187A, glandular hairs.
*Pedicel*.—2 mm long, with glandular hairs, Greyed Purple 187A.
*Bloom period*.—May in Canby, Oreg.

Flower bud:
*Size*.—2.5 mm wide and 4 mm long.
*Description*.—Glandular puberulent, ovoid, down facing.
*Color*.—Greyed Red 185A.

Flower:
*Type*.—Perfect.
*Shape*.—Campanulate.
*Size*.—7 mm long and 6 mm wide.
*Corolla description*.—5 petals, 3 mm long and 1 mm wide, spatulate, reflexed, margins entire, tip acute, glabrous on top and glandular on bottom side, White N155B.
*Calyx description*.—Campanulate, 6 mm long and 4 mm wide, with 5 lobes divided ½ way to the base, each 1.5 mm wide and 2.5 mm long, glandular hairs outside and some glabrous inside, tip obtuse, margin entire; color both sides Green Yellow 1C, outside tinted with Greyed Red 181A, but most strongly on the bottom half.
*Stamen description*.—5 in number, filaments 4 mm long, White N155B, anthers 0.5 mm, Orange 26A, pollen Orange 31A.
*Pistil description*.—1, 2-beaked, 4 mm long and 1.5 mm wide, Green Yellow 1A overall, ovary 1.5 mm long and 1.5 mm wide, style 2.5 mm long.
*Fragrance*.—None.
*Lastingness*.—Each thyrse blooms for about 3 weeks on the plant.

Fruit:
*Type*.—Two-beaked ovoid capsule.
*Fertility*.—Low.
*Color*.—Greyed Brown 199C.

Seed:
*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *